(12) United States Patent
Berger

(10) Patent No.: US 7,551,284 B2
(45) Date of Patent: Jun. 23, 2009

(54) METHOD AND DEVICE FOR THE OPTICAL MONITORING OF A RUNNING FIBER STRAND

(75) Inventor: Gerald Berger, Solingen (DE)

(73) Assignee: Saurer GmbH & Co. KG, Remscheid (DE)

( * ) Notice: Subject to any disclaimer, the term of this patent is extended or adjusted under 35 U.S.C. 154(b) by 569 days.

(21) Appl. No.: 10/584,815

(22) PCT Filed: Jan. 14, 2005

(86) PCT No.: PCT/EP2005/000292

§ 371 (c)(1),
(2), (4) Date: Jun. 27, 2006

(87) PCT Pub. No.: WO2005/068985

PCT Pub. Date: Jul. 28, 2005

(65) Prior Publication Data

US 2009/0002707 A1    Jan. 1, 2009

(30) Foreign Application Priority Data

Jan. 15, 2004  (DE) .................. 10 2004 002 047

(51) Int. Cl.
   *G01N 21/84* (2006.01)
(52) U.S. Cl. ........................... 356/430; 356/429
(58) Field of Classification Search .......... 356/429–430
   See application file for complete search history.

(56) References Cited

U.S. PATENT DOCUMENTS 5,835,656 A * 11/1998 Oishi et al. .................. 385/128
2005/0078306 A1 * 4/2005 Engels ..................... 356/238.3

FOREIGN PATENT DOCUMENTS

EP          0 643 294  A1    3/1995

* cited by examiner

*Primary Examiner*—Michael P Stafira
(74) *Attorney, Agent, or Firm*—K&L Gates LLP

(57) ABSTRACT

Disclosed are a method and a device for optically monitoring a running natural fiber strand. According to the invention, a light signal is sent onto the fiber strand and is emitted once again at a different point of the fiber strand surface, is received by a detector, and is evaluated so as to determine a foreign matter, thereby allowing light-guiding foreign matters to be distinguished from the non-light-guiding natural fibers.

15 Claims, 2 Drawing Sheets

METHOD AND DEVICE FOR THE OPTICAL MONITORING OF A RUNNING FIBER STRAND

CROSS-REFERENCES TO RELATED APPLICATIONS

This application claims the benefit of German patent application 10 2004 002 047.7, filed Jan. 15, 2004, herein incorporated by reference.

BACKGROUND OF THE INVENTION

The invention relates to a method for optically monitoring a running fiber strand made of natural fibers, and more particularly to such a method in which at least one light signal is transmitted onto the fiber strand and in which a light signal emitted by the fiber strand is received by a detector and is evaluated to determine a foreign substance made of synthetic material. The invention relates further to a device for carrying out such a method. A fiber strand in the context of the present invention is taken to mean a fiber band or a roving which are subsequently further processed to form a yarn, or else the yarn itself.

A generic method and a generic device are known, for example from European Patent Publication EP 0 643 294 A1.

During further processing of fiber materials, it is known that the presented fiber material may contain impurities in the form of foreign substances and foreign fibers, which can lead to undesired irregularities in the yarn produced therefrom and therefore also in the textiles produced in the subsequent processes. To avoid impurities of this type arriving in the yarn or the textile, the fiber strand is optically monitored. A method and a device are known for this purpose from European Patent Publication EP 0 643 294 A1, in which the fiber strand is acted upon by a light signal. The reflection signal generated by the fiber strand is guided to an image by means of a detector. The luminous intensity of the image is compared with a predetermined threshold value by means of evaluation electronics. The predetermined threshold value thus provides the limit value for a still acceptable impurity in the fiber strand. If this limit value is exceeded, a fault signal is generated in order to trigger a process intervention.

The known method and the known device are based on the fact that the foreign substances and foreign fibers are present with regard to their appearance in such a way that they have a clearly different reflection behavior of light signals compared to the fiber to be produced. In the cases in which, for example, foreign fibers or foreign substances of the same color are incorporated in the fiber strand, identification is not possible with the known methods and the known device.

SUMMARY OF THE INVENTION

The object of the invention is now to provide a method and device for monitoring a fiber strand made of natural fibers of the generic type, by means of which identification of foreign fibers which are of the same-color or transparent in the fiber strand is also possible.

This object is achieved according to the invention by a method and device for optically monitoring a running fiber strand made of natural fibers, in which at least one light signal from a light source is transmitted onto the fiber strand and in which a light signal emitted by the fiber strand is received by a detector and is evaluated by evaluation electronics to determine a foreign substance made of synthetic material. According to the invention, an output region for the light signal is scanned by the detector, which is arranged outside an input region, in which the light signal impinges on the fiber strand. The light signal is transmitted from the input region to the output region by the light-guiding properties of the foreign substance made of synthetic material.

Advantageous developments of the invention are defined by additional features and feature combinations of the method and the device.

The invention is based on the recognition that natural fibers, such as, for example cotton, in the microscopic structure consist of a cell composite. A fiber of this type is hardly in a position to guide a light signal because of the cell transitions. In comparison, synthetic substances or fibers have relatively good light conductivity, however. From this recognition, the invention provides that the light signal firstly impinges on the fiber strand in an input region, while the relayed light signal from the fiber strand is detected in an output region located outside the input region. The output light signal therefore indicates foreign fibers, which have a light conductivity and can therefore guide the input light signal out of the input region into the output region. The input region defines the zone in which the light signal impinges on the fiber strand. The output region denotes the zone, in which the relayed light signal is detected by a sensor, when it is output. For this purpose, the light source is directed onto the input region and the detector onto the output region.

The invention is therefore particularly suitable for identifying, in particular, foreign fibers made of synthetic material, such as polypropylene, which are generally used in practice as packaging material for the unspun natural fiber and can thus arrive, during unpacking, as a foreign component in the further processing of the natural fibers, in the spinning process.

As synthetic fibers have a smooth surface, these are not incorporated into the natural fiber composite like a natural fiber. Because of the lack of adhesion, a large number of kink positions occur along the only partially incorporated foreign fiber made of synthetic material, which lead to the input and output of the light signals. The input region and the output region can therefore be separated from one another. The regions can be arranged next to one another on the fiber strand at a spacing in the millimeter range and/or be offset with respect to one another at an angle which substantially also prevents touching or even overlapping of the regions. In this matter, very short fiber pieces can also be reliably identified. It is avoided by means of a minimum spacing between the input region and the output region, that reflection signals from the input region are also detected, which would influence the measuring result and therefore the reliable detection of foreign fibers. A spacing in the range of 0.5 mm to 5 mm has proven successful.

In order to obtain as high a luminous intensity as possible in the input region, the light signal is projected perpendicularly as a very narrow band onto the fiber strand. In this case, the light signal is preferably generated by a laser. The light band preferably has a width here of about 2 mm.

In order to easily determine the presence of a foreign substance, according to an advantageous development of the invention, the output light signal is received by a photocell. The luminous intensity of the output light signal is decisive here for determining the foreign fibers or foreign substance.

In order to detect, in this case, as narrowly limited a region as possible on the fiber strand, the photocell can be combined with an optical system, advantageously with a macrolens, by which the output region is defined on the fiber strand.

For reliable recognition of a foreign substance and in order to avoid the foreign substance arriving in the fiber end product, the luminous intensity measured is compared with a threshold value. Only when the threshold value is exceeded is a fault signal generated, which in turn triggers a process intervention, in particular a process interruption with subsequent elimination of the section of the fiber strand containing foreign fibers. For this purpose, the device according to the invention has evaluation electronics with a storage means and a computer means. The evaluation electronics can therefore be directly combined with a control mechanism, by means of which the production process is controlled.

The method according to the invention will be described in more detail hereinafter with the aid of an embodiment of the device according to the invention with reference to the accompanying figures.

DESCRIPTION OF THE PREFERRED EMBODIMENTS

Figure 1:
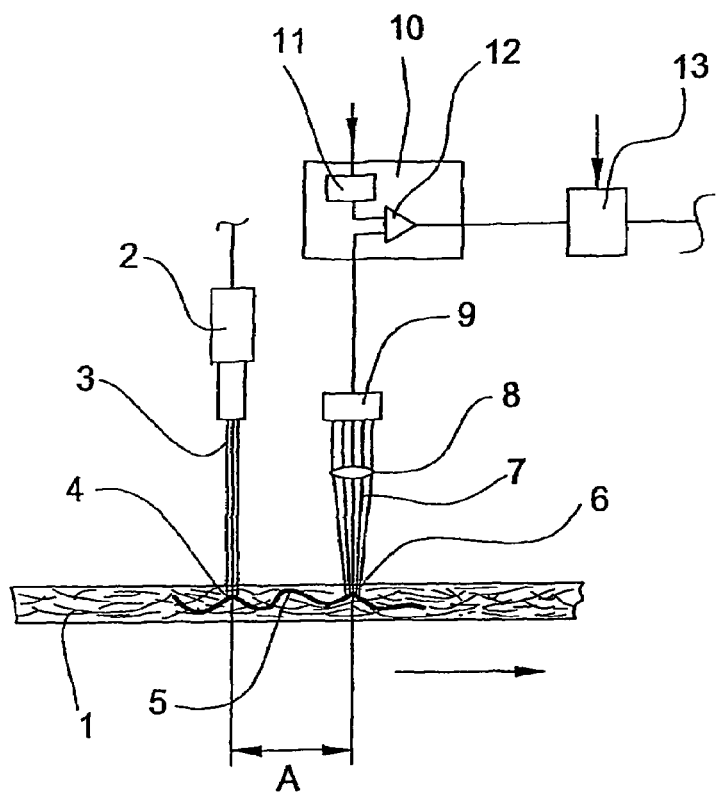
FIG. 1 schematically shows a first embodiment of the device according to the invention for carrying out the method according to the invention, FIG. 2 schematically shows a plan view of a fiber strand to be monitored, FIG. 3 schematically shows a further embodiment of the device according to the invention for carrying out the method according to the invention.

FIG. 1 schematically shows a first embodiment of the device according to the invention for carrying out the method according to the invention for optical monitoring of a fiber strand, by way of example, in the form of a fiber band. This fiber strand may alternatively be a yarn or thread.

The device has a light source 2, which is configured as a laser and which generates a bundled light signal 3 perpendicularly to the running fiber strand 1. The light signal 3 impinges on the surface of the fiber strand 1 in an input region 4.

An output region 6 is associated with the input region 4 at a spacing A in the running direction of the fiber strand 1. The output region 6 represents the zone on the fiber strand 1, onto which a detector 9 and an optical system 8 are directed for monitoring the fiber strand. The detector 9 is configured as a photocell, which is coupled to evaluation electronics 10. The evaluation electronics 10 contain a storage means 11 and computer means 12. The evaluation electronics 10 are connected to a control mechanism 13.

Figure 2:
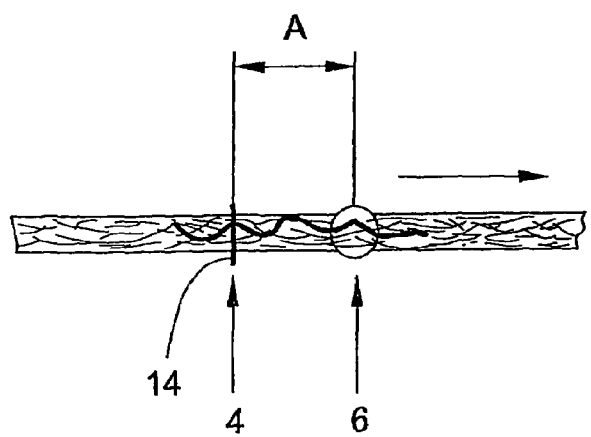

To describe the method according to the invention, reference is made below, in addition to FIG. 1, also to FIG. 2. FIG. 2 shows schematically here a plan view of the fiber strand 1 with a light signal which is projected onto the surface of the fiber strand 1 and shows, in the form of a light band 14, the input region 4. At a spacing next to the input region 4, the output region 6 adjusted by the optical system 8 is identified as a circle.

To monitor the running fiber strand 1, consisting of natural fibers, in a first position, a light signal 3 generated by a light source 2 is projected onto the surface of the fiber strand 1. This position is denoted an input region 4, in which the light signal 3 is input into the fiber composite of the fiber strand 1. If the fiber strand 1 contains a foreign fiber 5 made of synthetic material, a light quantity also arrives from the light signal 3 into the foreign fiber 5. The light is preferably input at kink positions or edges of the foreign fiber and relayed by the foreign fiber. The light inside the foreign fiber 5 thus arrives at the output region 6 arranged at a spacing A. Perpendicularly to the fiber strand 1, the output region 6 is scanned by the optical system 8 and the detector 9. The optical system 8 is preferably formed by a macrolens in order to obtain as small as possible an observation region covering the fiber strand with respect to its thickness. The size of the output region depends in this case on the thickness of the fiber strand. Owing to the kink positions contained in the foreign fiber 5, light waves are output, which arrive at the detector 9 from the output region 6. The detector 9 is configured as a photocell in order to receive and evaluate the output light signals. The spacing A between the input region 4 and the output region 6 is about 1 mm. This is the distance over which the light has to be guided. The spacing may, depending on the circumstance and the size of the foreign fibers to be detected, may be 0.5 mm to 5 mm or more.

To evaluate the light signals detected by the photocell, the detector 9 is linked to the evaluation electronics 10. The threshold value is filed in the storage means 11 of the evaluation electronics 10. The threshold value is, in this case, an acceptable luminous intensity, which is used as a limit value to identify a foreign substance. The measured signal emitted by the detector and the threshold value are compared with one another in the computer means 12, which may be formed, for example, by a comparator. When the threshold value is exceeded, a fault signal is generated, which is relayed by the evaluation electronics directly to the control mechanism 13. Inside the control mechanism 13, the fault signal leads to the triggering of a process change, in particular an interruption of the fiber strand with a subsequent elimination of the fault position. It is thus ensured that the fiber section with the foreign fiber does not reach the end product.

In the embodiment shown in FIG. 1, the light source and the detector are arranged in one plane with the longitudinal axis of the fiber strand and, for example, combined in one unit. Because of the generally non-uniform and irregular course of the foreign fiber, the input and output of the light signals is ensured. To improve the input or output effect, however, the light source and the detector may be arranged at an angle differing from 90° with respect to the running direction of the fiber strand. Furthermore, the use of a laser as a light source and a photocell as a detector in the embodiment according to FIG. 1 is by way of an example. Basically, other light-emitting optical systems can be used, which have a divergence towards zero in order to project light signals onto the surface of the fiber strand. Line sensors can also advantageously be used as detectors.

Figure 3:
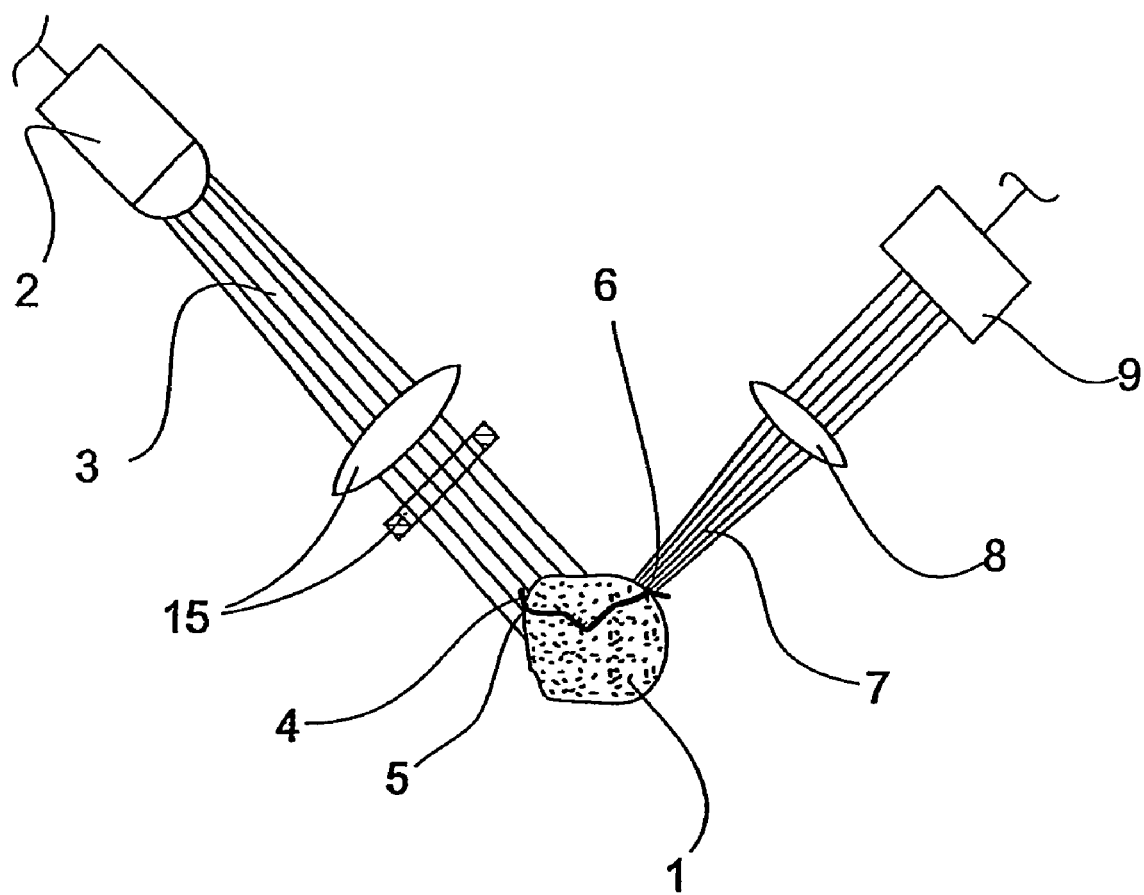

A further embodiment of the device according to the invention for carrying out the method according to the invention is shown schematically in FIG. 3. A schematic view transverse to the fiber running direction is shown here. The fiber strand 1 is shown here in a cross-sectional view, which is the same as the drawing plane. To generate a light signal 3, a light-emitting diode is provided here, for example. In order, as far as possible, to generate a light band with a high intensity on the surface of the fiber strand 1, an optical system 15, consisting of a lens and a shutter, is present. In this case, the light signals 3 impinge on the fiber strand 1 in the input region 4.

The optical axis of the output region 6 is, however, offset by an angle with respect to the optical axis of the input region 3. An optical system 8, for example in the form of a macrolens, and a detector 9, for example in the form of a photocell, are associated with the output region 6.

The functioning of the device shown in FIG. 3 is identical to the preceding embodiment, so reference is made to the preceding description at this point. In the embodiment shown in FIG. 3, a smaller spacing may also be present, in addition, between the input region and the output region in the longitudinal direction of the fiber strand. The angular offset between the optical axes allows a very compact mode of construction.

The method according to the invention and the device according to the invention have the particular advantage, that, especially in the processing of natural fibers, the foreign fiber components released from the packaging material can be reliably identified and eliminated, even when they are transparent or do not differ with regard to their colour from the natural fibers. Interwoven fabrics made of film tapes, preferably made of polypropylene, are used as packaging. Owing to the light conductivity of the PP fiber, identification with a high degree of certainty is possible in the monitoring of the fiber strand. In principle, every light spot which is visible within the output region can be identified as a foreign substance.

What is claimed is:

1. Method for optically monitoring a running fiber strand made of natural fibers, in which at least one light signal is transmitted onto the fiber strand and in which a light signal emitted by the fiber strand is received by a detector and is evaluated to determine a foreign substance made of synthetic material, characterized in that an output region for the light signal is scanned by the detector, which is arranged outside an input region, in which the light signal impinges on the fiber strand, the light signal being transmitted from the input region to the output region by the light-guiding properties of the foreign substance made of synthetic material.

2. Method according to claim 1, characterized in that the light signal impinges on the fiber strand in the input region with a spacing of a few millimeters from the output region.

3. Method according to claim 2, characterized in that the light signal is projected as a very narrow band, lying transversely to the fiber strand, onto the surface of the fiber strand.

4. Method according to claim 1, characterized in that the light signal is generated by a laser, which projects a bundled light signal in the input region onto the fiber strand.

5. Method according to claim 1, characterized in that the light signal is received by a photocell, the luminous intensity of the signal being evaluated to determine the foreign substance.

6. Method according to claim 5, characterized in that the measured luminous intensity is compared with a threshold value for evaluation, in that a fault signal is generated when the threshold value is exceeded and in that the fault signal triggers a process intervention.

7. Method according to claim 1, characterized in that the size of the output region is determined by an optical system associated with the photocell.

8. Device for optically monitoring a running fiber strand made of natural fibers, illuminated by a light source (2), with a detector (9) for receiving a light signal (7) emitted by the fiber strand (1) and with evaluation electronics (10) connected to the detector (9) for determining a foreign substance (5) made of synthetic material, characterized in that the light source (2) is directed onto an input region (4), in which the light signal (3) impinges on the fiber strand (1), in that the detector (9) is directed onto an output region (6) to receive the transmitted light signal (7), and in that the input region (4) and the output region (6) are separated from one another.

9. Device according to claim 8, characterized in that a spacing A is provided between the input region (4) of the light signal (3) and the output region (6) of the light signal (7).

10. Device according to claim 8, characterized in that the spacing is in the region of 0.5 mm to 5 mm.

11. Device according to claim 8, characterized in that the light source (2) is provided such that the light signal (3) can be projected as a very narrow band (14) lying transversely to the running direction of the fiber band (1).

12. Device according to claim 11, characterized in that the light source is configured as a laser (2).

13. Device according to claim 8, characterized in that the detector (9) is formed by a photocell, by which the luminous intensity of the signal (7) is detected.

14. Device according to claim 13, characterized in that an optical system (8) is associated with the photocell (9) and in that the optical system (8) has at least one macrolens, by which the output region (7) is determined.

15. Device according to claim 8, characterized in that the evaluation electronics (10) have a storage means (11) for receiving a threshold value for the luminous intensity and computer means (12) for determining a fault signal for identifying a foreign substance.

* * * * *